(12) United States Patent
Weschler

(10) Patent No.: US 7,056,537 B2
(45) Date of Patent: Jun. 6, 2006

(54) TREATMENT OF LANDFILL GAS

(75) Inventor: Richard Weschler, Brooklyn, NY (US)

(73) Assignee: Aceto Corporation, Lake Success, NY (US)

( * ) Notice: Subject to any disclaimer, the term of this patent is extended or adjusted under 35 U.S.C. 154(b) by 106 days.

(21) Appl. No.: 10/799,434

(22) Filed: Mar. 11, 2004

(65) Prior Publication Data

US 2005/0084475 A1    Apr. 21, 2005

Related U.S. Application Data

(60) Provisional application No. 60/512,327, filed on Oct. 17, 2003.

(51) Int. Cl.
*A61L 9/00*        (2006.01)
*A61L 9/01*        (2006.01)
*A61L 9/014*       (2006.01)
*B01D 53/02*       (2006.01)
*B01D 53/14*       (2006.01)
*A01N 59/00*       (2006.01)
*A01N 59/16*       (2006.01)
*A01N 59/20*       (2006.01)

(52) U.S. Cl. ............... 424/619; 424/76.1; 424/76.5; 424/76.8; 424/76.9; 424/417; 424/490; 424/600; 424/618; 424/630; 424/637; 424/638; 424/641; 424/646; 424/647; 424/725; 424/742; 424/745; 424/774; 514/699; 514/703; 514/739; 514/770; 502/62; 502/80; 502/84; 502/406; 502/517; 95/136

(58) Field of Classification Search ........... 424/76.5, 424/76.8, 76.9, 600, 618–619, 630, 637–638, 424/641, 646, 647, 725, 742, 774, 76.1, 417, 424/490, 745; 514/699, 770, 703, 739; 502/84, 502/406, 517, 62, 80; 95/136
See application file for complete search history.

(56) References Cited

U.S. PATENT DOCUMENTS

| | | | |
|---|---|---|---|
| 4,089,945 A | * | 5/1978 | Brinkman et al. .......... 424/702 |
| 2005/0005869 A1 | * | 1/2005 | Fritter et al. .............. 119/173 |
| 2005/0175577 A1 | * | 8/2005 | Jenkins et al. ............ 424/76.1 |

FOREIGN PATENT DOCUMENTS

| | | | |
|---|---|---|---|
| CA | 1067627 | * | 12/1979 |
| JP | 3-157134 | * | 7/1991 |

OTHER PUBLICATIONS

HCAPLUS Abstract, 115:214022/DN; abstracting JP 3-157134 (1991).*

* cited by examiner

*Primary Examiner*—John Pak
(74) *Attorney, Agent, or Firm*—Stroock & Stroock & Lavan LLP

(57) ABSTRACT

The present invention relates to a method of abating hydrogen sulfide gas emitted by or generated in landfills. Certain embodiments of the present invention relate to contacting hydrogen sulfide gas with Fuller's earth or other carrier materials and metals such as silver, copper, iron, zinc or mixtures thereof, and other components.

15 Claims, No Drawings

TREATMENT OF LANDFILL GAS

This application claims priority to U.S. Provisional Patent Application No. 60/512,327 filed Oct. 17, 2003 under 35 U.S.C. 119(e).

BACKGROUND OF INVENTION

The invention relates to the abatement of toxic and/or noxious gases, particularly the abatement of hydrogen sulfide gas emitted by or generated in landfills.

Hydrogen sulfide is a flammable, poisonous gas with a characteristic offensive odor of rotten eggs. In high concentrations, $H_2S$ can be extremely hazardous. At concentrations of greater than about 500 ppm, hydrogen sulfide can be fatal to humans.

Hydrogen sulfide gas can be released by various sources such as coal pits, gas wells, sulfur springs and decaying organic matter. Hydrogen sulfide generated by decaying organic matter is generally the product of anaerobic digestion, and can be released by solid waste landfills, sewage treatment facilities, paper mill waste, cattle feed lots, poultry farms, and other industries employing anaerobic digestion for processing. Anaerobic digestion takes place in the absence of oxygen resulting in the formation of methane ($CH_4$), ammonia ($NH_3$), hydrogen sulfide ($H_2S$) and phosphine ($PH_3$).

Landfills are sometimes located within close proximity to residential areas. Such close proximity creates the potential of exposure to hazardous conditions such as gas emissions. As such, there exists a need to abate toxic and offensive gases such as hydrogen sulfide gas that are generated.

SUMMARY OF INVENTION

The present invention relates to a method of abating hydrogen sulfide gas emitted by landfills and other sources. Certain embodiments of the present invention relate to contacting hydrogen sulfide gas with metals such as silver, copper, iron, zinc or mixtures and salts thereof, and other components, which can be combined with carrier materials, such as Fuller's earth (described below). One embodiment of the invention relates to the use of Fuller's earth, $AgNO_3$, $Fe_2(SO_4)_3$ or other metal compounds of general formula $Me_x(SO_4)_y$ or $Me_x(NO_3)_y$, alone or mixed with carrier material, applied in and/or over a landfill and/or mixed with fill prior to its deposit on a landfill. In one embodiment of the invention, the hydrogen sulfide abating material is added in layers.

It is advantageous to combine these and other metal containing materials with carrier materials, such as Fuller's earth, clay, diatomaceous earth, zeolite material, activated charcoal, alumina, silica, aluminum silicate, magnesium aluminum silicate, magnesium silicate and other porous or high surface area materials. This can increase surface contact between the hydrogen sulfide gas and the metals and provide other benefits, such as improving reaction kinetics. Combinations of the metal containing materials with Fuller's earth are particularly preferred. The combinations discussed above, of carrier or porous materials, with an amount of aforementioned metal containing materials, increases the removal efficiency for hydrogen sulfide gas than the use of either component alone.

Fuller's Earth is a naturally occurring sedimentary clay composed mainly of alumina, silica, iron oxides, lime, magnesia and water in variable proportions. As used herein, it also includes magnesium silicates and aluminum silicates having similar properties. Other types of clay materials that could be used are ball clay, bentonite, fire clay and kaolin to name a few.

Still other objects and advantages of the invention will in part be obvious and will in part be apparent from the specification.

The invention accordingly comprises the several steps and the relation of one or more of such steps with respect to each of the others, and the composition of matter embodying features of construction, combination(s) of elements and arrangement of parts which are adapted to effect such steps, all as exemplified in the following detailed disclosure, and the scope of the invention will be indicated in the claims.

DETAILED DESCRIPTION OF THE PREFERRED EMBODIMENTS

It has been determined that hydrogen sulfide gas emitted by or generated in landfills may be treated with a mixture of components to abate its offensive odors and neutralize its toxicity to surrounding communities. Abatement of the hydrogen sulfide gas is such that the gas is emitted at a concentration less than 10 ppb.

In one embodiment of the invention, hydrogen sulfide gas, mercaptan and sulfur components are abated with silver nitrate and/or silver nitrate solution. This is preferably combined with Fuller's earth, magnesium aluminum silicate, aluminum silicate or magnesium silicate, and combinations thereof; plus, optionally, any of eucalyptus, benzaldehyde and citronella. Other carrier materials as identified above are also useful.

In another embodiment of the invention, hydrogen sulfide gas is abated with ferric sulfate and/or ferric sulfate solution. This is preferably combined with Fuller's earth, magnesium aluminum silicate, aluminum silicate or magnesium silicate, and combinations thereof; plus, any of benzaldehyde and citronella.

In another embodiment of the invention, hydrogen sulfide gas is abated with copper sulfate and/or copper sulfate solution. This is preferably combined with Fuller's earth, magnesium aluminum silicate, aluminum silicate or magnesium silicate, and combinations thereof; plus any of benzaldehyde and citronella.

In another embodiment of the invention, hydrogen sulfide gas is abated with a solution of silver nitrate and/or a solution of zinc sulfate. This is preferably combined with Fuller's earth, magnesium aluminum silicate, aluminum silicate or magnesium silicate, and combinations thereof; plus any of benzaldehyde and citronella.

In yet another embodiment of the invention, hydrogen sulfide gas is abated with a solution of silver nitrate and/or a solution of zinc sulfate. This is preferably combined with Fuller's earth, magnesium aluminum silicate, aluminum silicate or magnesium silicate, and combinations thereof.

The amount of metals such as silver, copper, iron, zinc or mixtures and salts thereof, used in the present invention are typically in the range from about 1 ppm to about 5,000 ppm, preferably in the range from about 10 ppm to about 500 ppm, with the remainder as a carrier, preferably a silicate carrier and other additives. The silicate carrier is preferably included in the range from about 70% wt. to about 85% wt.

Compositions for abating landfill gas can be represented by, but are not limited to, the following examples, which are not intended to be construed as limiting.

EXAMPLE 1

| Component | Amount |
|---|---|
| Fuller's Earth | 85% |
| Fragrance | 1–2% |
| Benzaldehyde | 1–4% |
| Citronella | 0.25% |
| Water | 11–13% |
| Silver Nitrate | 300 ppm |

EXAMPLE 2

| Component | Amount |
|---|---|
| Fuller's Earth | 74% |
| Eucalyptus 80/85 | 2% |
| Lemon PK-97 | 0.45% |
| Citronella | 0.10% |
| Water | 10–15% |
| Silver Nitrate | 300 ppm |

EXAMPLE 3

| Component | Amount |
|---|---|
| Fuller's Earth | 85% |
| Cherry Fragrance | 2% |
| Benzaldehyde | 4% |
| Citronella | 0.25% |
| Water | 10–15% |
| Zinc Sulfate | 2,500–3,000 ppm |
| Silver Nitrate | 100 ppm |

EXAMPLE 4

| Component | Amount |
|---|---|
| Fuller's Earth | 80% |
| Water | 10–20% |
| Zinc Sulfate | 2,500 ppm |
| Silver Nitrate | 100 ppm |

EXAMPLE 5

| Component | Amount |
|---|---|
| Fuller's Earth | 80% |
| Water | 15–20% |
| Ferric Sulfate | 2,500–5,000 ppm |
| Cherry Fragrance | 2% |
| Benzaldehyde | 2–4% |
| Citronella | 0.25% |

EXAMPLE 6

$H_2S$ Abatement

Tests were performed using 195 grams of the composition of Example 3 to treat various combinations of $H_2S$ concentration and flow rate. Hydrogen sulfide gas was prepared at selected concentrations in a gas bag and was pumped through a column reactor at a controlled flow rate using a peristaltic pump. The effluent gas was passed through an absorbing solution trap (impingers) where hydrogen sulfide was absorbed by alkaline cadmium hydroxide solution. The absorbed sulfide was subsequently determined by spectrophotometric measurement of the methylene blue produced from sulfide in a color development procedure. The hydrogen sulfide determination procedure was based on the method provided in "Methods of Air Sampling and Analysis" by James P. Loage, inporated herein by reference. Out method detection limit was 10 ppb.

Experimental results are presented in Table 1. The test was conducted under dry conditions.

TABLE 1

Experimental Results of 1st Column Reactor Test

| Run | Feed Conc. (ppm) | Feed Vol. (Liter) | Flow Rate (L/min) | $H_2S$ Mass Loading (μg) | Cumulative $H_2S$ Mass loaded (μg) | Mass Loading Rate (μg/min) | $H_2S$ Mass in Effluent (μg) | $H_2S$ Conc. in Effluent (ppm) | Cumulative $H_2S$ Mass Removed by Column (μg) |
|---|---|---|---|---|---|---|---|---|---|
| 1 | 10 | 30 | 0.78 | 420 | 420 | 11 | ND | ND | 420 |
| 2 | 10 | 30 | 0.78 | 420 | 840 | 11 | ND | ND | 840 |
| 3 | 50 | 30 | 0.78 | 2,100 | 2,940 | 55 | ND | ND | 2,940 |
| 4 | 50 | 30 | 0.46 | 2,100 | 5,040 | 32 | ND | ND | 5,040 |
| 5 | 100 | 30 | 0.46 | 4,200 | 9,240 | 64 | ND | ND | 9,240 |
| 6 | 100 | 30 | 0.78 | 4,200 | 13,440 | 109 | ND | ND | 13,440 |
| 7 | 250 | 20 | 0.46 | 7,000 | 20,440 | 161 | ND | ND | 20,440 |
| 8 | 500 | 20 | 0.46 | 14,000 | 34,440 | 322 | 4 | 0.15 | 34,436 |
| 9 | 500 | 30 | 0.78 | 21,000 | 55,440 | 546 | 423 | 10.08 | 55,017 |
| 10 | 100 | 20 | 0.78 | 2,800 | 58,240 | 109 | 15 | 0.54 | 58,225 |
| 11 | 500 | 30 | 0.78 | 21,000 | 79,240 | 546 | 2,160 | 51.43 | 77,080 |
| 12 | 500 | 20 | 0.46 | 14,000 | 93,240 | 322 | 420 | 14.99 | 92,820 |
| 13 | 500 | 30 | 0.78 | 21,000 | 114,240 | 546 | 2,226 | 53.01 | 112,014 |

TABLE 1-continued

Experimental Results of 1st Column Reactor Test

| Run | Feed Conc. (ppm) | Feed Vol. (Liter) | Flow Rate (L/min) | $H_2S$ Mass Loading (μg) | Cumulative $H_2S$ Mass loaded (μg) | Mass Loading Rate (μg/min) | $H_2S$ Mass in Effluent (μg) | $H_2S$ Conc. in Effluent (ppm) | Cumulative $H_2S$ Mass Removed by Column (μg) |
|---|---|---|---|---|---|---|---|---|---|
| 14 | 500 | 20 | 0.46 | 14,000 | 128,240 | 322 | 411 | 14.68 | 127,829 |
| 15 | 500 | 10 | 0.28 | 7,000 | 135,240 | 196 | 470 | 33.56 | 134,770 |
| 16 | 100 | 20 | 0.46 | 2,800 | 138,040 | 64 | 90 | 3.20 | 137,950 |

The results showed that the column could remove hydrogen sulfide to below detection limit of 10 ppb for at least 20 mg of hydrogen sulfide. After a cumulative mass loading of 34.4 mg of hydrogen sulfide (test run #8), level above the reported odor threshold (i.e. 5 to 10 ppb) in the effluent was suspected.

After test run #8, the column's performance in hydrogen sulfide removal seemed to depend on the mass loading rate (μg/min). Test run #9 with a high mass loading rate of 546 μg/min resulted in 10 ppm of effluent concentration which is the NIOSH exposure limit. However, test run #10 with a lower mass loading rate of 109 μg/min resulted in a much lower effluent concentration (0.54 ppm). It should be noted that 0.54 ppm is still above the odor threshold.

It was observed that the column can effectively control hydrogen sulfide at a dosage rate between 20 mg to 34 mg $H_2S$ per 195 gram of composition used. This translates to 0.1 to 0.17 mg $H_2S$/g of composition. Suitable compositions in accordance with the invention are able to eliminate over 0.01 mg $H_2S$, preferably 0.05 mg $H_2S$ per gram of composition.

Application methods for using the compositions include, but are not limited to, a layering approach and a mixing approach. In the layering approach, a layer of any combination of the compositions in the Examples is applied onto the surface of a landfill. To ensure adequate performance, the layer has a minimum thickness of 2 cm. Layer thickness may vary based on $H_2S$ concentrations at different landfills. In the mixing approach, any combination of the compositions in the Examples is mixed with landfill material and applied to the surface of a landfill.

Compositions for abating landfill gas are advantageously made by mixing Fuller's earth with a metal compound. Upon mixing, the Fuller's earth is coated with the metal compound to form a uniform granular mixture. The approximate average granular size of the mixture is advantageously in the range from about 1 mm to about 8 mm in diameter, preferably from about 3 mm to about 6 mm in diameter. Larger particle sizes can lessen the amount of dust created in application. The uniform granular mixture advantageously has a specific gravity from about 0.70 to about 0.85.

Using a minimum average thickness of 2 cm and using, as a basis, a landfill with a surface area of 250 acres, the composition in the layer of mixture to be applied at a landfill can comprise from about 65 to about 75 tons of composition per acre of landfill. The metal concentration in the layer is advantageously from about 0.1 tons to about 2.5 tons of metal in per acre of landfill.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is understood to be that the following claims are intended to cover all of the generic and specific features of the invention herein described and all statements of the scope of the invention which, as a matter of language, might be said to fall there between.

Particularly, it is understood that in said claims, compounds recited in the singular are intended to include compatible mixtures of such compounds wherever the sense permits.

What is claimed is:

1. A composition for abating hydrogen sulfide emissions comprising: a combination of Fuller's earth and a metal compound formulated to eliminate at least 0.01 grams of $H_2S$ per gram of composition; a fragrance, benzaldehyde, citronella, eucalyptus and water.

2. The composition of claim 1, wherein the fragrance is present in an amount from about 1% wt. to about 2% wt.

3. The composition of claim 1, wherein the benzaldehyde is present in an amount from about 1% wt. to 4% wt.

4. A method of reducing landfill gas, comprising:
   mixing a composition formed by combining Fuller's earth and a metal compound formulated to eliminate at least 0.01 grams of $H_2S$ per gram of composition with landfill material and applying the mixture to the surface of a landfill.

5. The method of claim 4, wherein the metal compound is silver nitrate or silver nitrate solution.

6. The method of claim 4, wherein the metal compound is ferric sulfate or ferric sulfate solution.

7. The method of claim 4, wherein the metal compound is copper sulfate or copper sulfate solution.

8. The method of claim 4, wherein the metal compound is a mixture of silver nitrate and zinc sulfate solutions.

9. The method of claim 4, wherein the Fuller's earth is comprised of magnesium silicate, aluminum silicate or combinations thereof.

10. The method of claim 4, wherein the metal compound is present in the composition in an amount from about 1 ppm to about 5,000 ppm.

11. The method of claim 4, wherein the Fuller's earth is present in an amount from about 70% wt. to about 85% wt.

12. A method of reducing landfill gas, comprising:
   applying a layer of a composition formed by combining Fuller's earth and a metal compound formulated to eliminate at least 0.01 grams of $H_2S$ per gram of composition on the surface of a landfill, wherein said layer has a minimum average thickness of 2 cm.

13. The method of claim 12, wherein the layer comprises at least about 65 tons of the composition per acre of landfill.

14. The method of claim 12, wherein the layer comprises from about 65 tons to 75 tons of the composition per acre of landfill.

15. The method of claim 12, wherein the composition further comprises a fragrance, benzaldehyde, citronella, eucalyptus and water.

* * * * *